(12) United States Patent
Yadav et al.

(10) Patent No.: US 7,618,363 B2
(45) Date of Patent: Nov. 17, 2009

(54) HYDRAULICALLY ACTUATED ARTIFICIAL MUSCLE FOR VENTRICULAR ASSIST

(75) Inventors: Jay Yadav, Hunting Valley, OH (US); Mark Allen, Atlanta, GA (US); David O'Brien, Norcross, GA (US); David Stern, Grayson, GA (US); Jason White, Atlanta, GA (US); Michael A. Fonseca, Marietta, GA (US)

(73) Assignee: CardioMEMS, Inc., Atlanta, GA (US)

( * ) Notice: Subject to any disclaimer, the term of this patent is extended or adjusted under 35 U.S.C. 154(b) by 149 days.

(21) Appl. No.: 10/636,293

(22) Filed: Aug. 6, 2003

(65) Prior Publication Data

US 2004/0092790 A1    May 13, 2004

Related U.S. Application Data

(60) Provisional application No. 60/401,378, filed on Aug. 6, 2002.

(51) Int. Cl.
*A61M 1/12* (2006.01)
(52) U.S. Cl. ....................................................... 600/16
(58) Field of Classification Search .................. 600/16, 600/17
See application file for complete search history.

(56) References Cited

U.S. PATENT DOCUMENTS

| 5,713,954 | A | * | 2/1998 | Rosenberg et al. | 600/17 |
|---|---|---|---|---|---|
| 6,266,564 | B1 | | 7/2001 | Hill et al. | |
| 6,293,906 | B1 | * | 9/2001 | Vanden Hoek et al. | 600/16 |
| 6,602,182 | B1 | * | 8/2003 | Milbocker | 600/16 |
| 6,616,596 | B1 | * | 9/2003 | Milbocker | 600/16 |

* cited by examiner

*Primary Examiner*—George R Evanisko
*Assistant Examiner*—Alyssa M Alter
(74) *Attorney, Agent, or Firm*—Kilpatrick Stockton LLP

(57) ABSTRACT

A ventricular assist device comprises a sheet of hydraulically actuated material that can be affixed to prescribed locations on the surface of the heart to assist areas of the heart that do not contract normally. The material is comprised of a network of contractible unit cells that individually contract when fluid is pumped into them. These unit cells are connected together in a network that causes the sheet to contract radially inward. This contraction causes the sheet to transmit forces to the heart to assist in its natural contraction. A sensing function coordinates the contraction of the sheet with the contraction of the heart. The change in shape of the device is accomplished by distributing pressurized fluid throughout the spaces of the device by way of a network of channels. When pressure is removed from the fluid system, it assumes a deenergized "rest" position in which it does not transmit any forces to the surface of the heart. This property of the device prevents the device from inhibiting the heart's natural contractions in the event of a failure of the device or a loss of hydraulic power.

23 Claims, 9 Drawing Sheets

HYDRAULICALLY ACTUATED ARTIFICIAL MUSCLE FOR VENTRICULAR ASSIST

CROSS-REFERENCE TO RELATED APPLICATION

This application claims the priority of U.S. Provisional Patent Application Ser. No. 60/401,378, filed Aug. 6, 2002.

TECHNICAL FIELD

The invention relates to implantable cardiac assist systems and more particularly to a hydraulic implantable system that can apply a controlled spatial and temporal distribution of forces and pressures to portions of the heart surface to aid it in its natural function.

BACKGROUND OF THE INVENTION

Many of the pathologies of the heart lead to a deterioration in its ability to pump blood. In this situation, the heart itself and the organs of the body are at great risk for sustaining irreversible damage. Ventricular assist devices can be implanted to ensure that the organs of the body are supplied with an adequate flow of blood by taking over the pumping action of the heart. Ventricular assist devices can help heart transplant patients survive until a suitable donor heart is found. They can also help the heart return to normal function after heart surgery. Or they can be used as permanent devices in cases of severe heart failure where heart transplantation is not a viable option for the patient.

Most commonly used ventricular assist devices are pumping devices, which shunt blood from the left ventricle of the heart to the aorta. Use of a ventricular assist pump was shown to help promote improved heart function in some patients with heart failure. The most significant problem that patients with ventricular assist pumps face stems from the fact that the patient's blood is constantly circulated through the man-made surfaces of the device. This frequent contact with the surface of the device increases the likelihood that components of the patient's blood will react to the presence of a foreign object and result in blood clots, infections, and immune system reactions.

Another type of ventricular assist devices consists of an assembly that serves to apply pressure to the surface of the heart in order to augment or replace its pumping action. This type of device has the advantage of minimal contact with the patient's blood, and so the risk of blood clots, infections and immune system reactions is significantly reduced. The drawback of this type of device is that repeated cycling of pressure to the exterior of the heart can, lead to mechanical trauma to the surface of the heart. In addition, these types of devices do not localize the pressure to the damaged area of the heart but also apply pressure to healthy areas of the heart.

Thus there is a need to supply mechanical energy in a localized fashion to the non-functional portions of the heart muscle, thereby minimizing the potential to traumatize otherwise healthy portions of the heart, as well as minimizing the total energy required to restore the patient's heart function.

"Smart skin" or artificial muscle could in theory be used to cover the nonfunctional area of the heart and restore functionality. However, a challenge in implementing this approach is the ability to distribute sufficient energy and power in the artificial muscle, especially on the relatively small scales of interest, since in many cases the nonfunctional areas of the heart are on the order of only tens of millimeters in diameter.

Any assist device must have sufficient energy and power density in order for it to perform the work necessary to aid in circulating blood. A critical issue is whether the energy or power can be distributed in an appropriate fashion throughout the volume of the device, especially as the total physical size of the device scales down. Although electrical energy can be easily dispersed throughout the volume of a ventricular assist device, conversion of this electrical energy to mechanical energy by means of a multiplicity of small-scale-localized actuators is difficult, due to the unfavorable scaling of many of these actuators. Magnetic and electrostatic actuators cannot supply sufficient energy density for this type of device on the small scale. Piezoelectric actuators can supply the required energy density but must utilize very high electric potentials, a condition that is not ideal for biocompatibility. Shape memory alloys can also supply the required energy density but require heating and cooling cycling which would not be good for the heart, and in addition may not be able to withstand the cycling of the heart without undergoing fatigue-based failure. Thus none of these types of actuating mechanisms are well suited to the demands of a ventricular assist device.

Still another consideration in the design of a ventricular assist device is the fact that, if the device were to fail, the presence of the failed ventricular assist device should not increase the demands on a partially dysfunctional heart. If the device fails and the heart has to pump against the failed device, heart failure is rendered more likely. Thus a desirable characteristic of a ventricular assist device is that, if it were to fail, it should place a neutral demand on the unassisted heart and so not contribute to adverse clinical consequences.

SUMMARY OF THE INVENTION

Hydraulic energy is a reliable mechanical energy distribution approach with the required energy density that is a good candidate for a ventricular assist system. Therefore, an attractive approach is to utilize larger scale (e.g., cm-scale) electrical-to-mechanical energy conversion where the required forces are available in, e.g., magnetic actuators, and then distribute this mechanical power by means of hydraulics to the artificial muscle. Such microhydraulics can then form the basis of the actuation of the artificial-muscle-based ventricular assist device.

Microhydraulic technology has several advantages for use in a ventricular assist system. First, it does not require detailed computer control technology. Additionally, the device can cycle between two different conformations: one being a pressurized or "energized" form, and another being the depressurized or "de-energized" form. The shapes of these two forms can be prescribed by the device's internal microhydraulic geometry. Lastly, the device could be specifically designed on a patient-by-patient basis in much the same way that eyeglasses are prescribed according to the measured eyesight of the patient.

This invention thus relates to an implantable cardiac assist system that utilizes hydraulics to actuate a material that can supply forces and pressures to portions of the surface of the heart. The device consists of a sheet of hydraulically actuated material which is comprised of a network of mechanically-linked contractile unit cells that can individually be filled with fluid or emptied of fluid. The physical arrangement and interconnection of the unit cells prescribes the overall motion and force application of the device. Each unit cell is comprised of, e.g., a central actuating cavity inside an expandable membrane. In some cases, natural elastic forces define the contracted shape of the membrane, and expanded, pressurized unit cells reorganize the shape of the membrane to define the expanded form of the membrane. In a preferred embodiment, the pressurized device is in its most contractile position, and the relaxed, unpressurized device is in its most expanded position, so as to not place additional strain on the heart in the event of device failure.

Objects, features, and advantages of the present invention will become apparent upon reading the following specification, when taken in conjunction with the drawings and the appended claims.

DETAILED DESCRIPTION OF THE DISCLOSED EMBODIMENT

Figure 1:
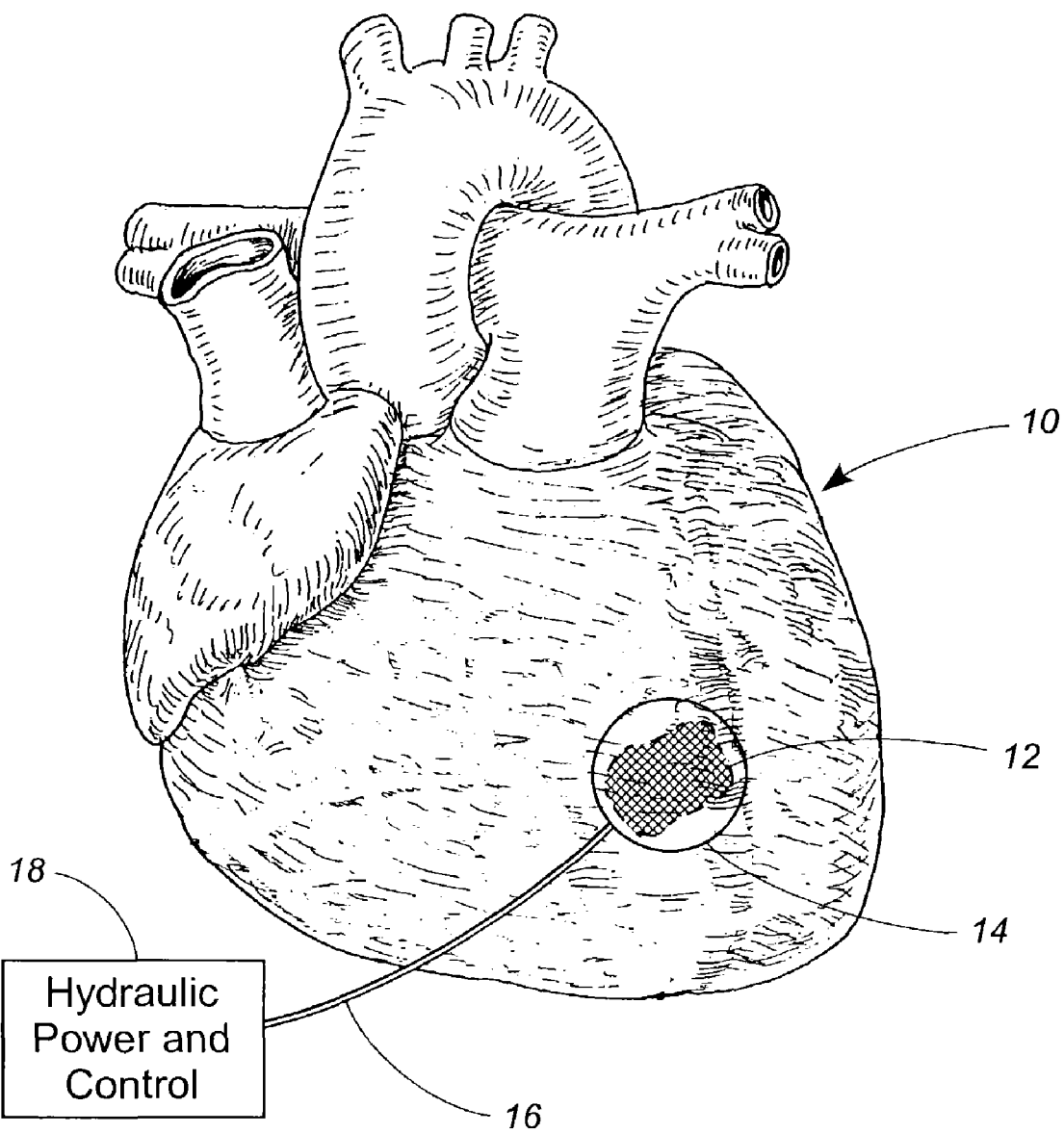
FIG. 1 is a perspective view of a ventricular assist device according to a disclosed embodiment of the present invention implanted over a diseased portion of a heart.

Referring now to the drawings, in which like numerals indicate like elements throughout the several views, FIG. 1 shows a heart 10 with a diseased area 12 on its left ventricle. A ventricular assist device 14 is attached to the heart 10 over the diseased area 12 of the left ventricle. A length of tubing 16 connects the ventricular assist device 14 to a source of hydraulic power and control 18, as will be more particularly described below.

Figure 2:
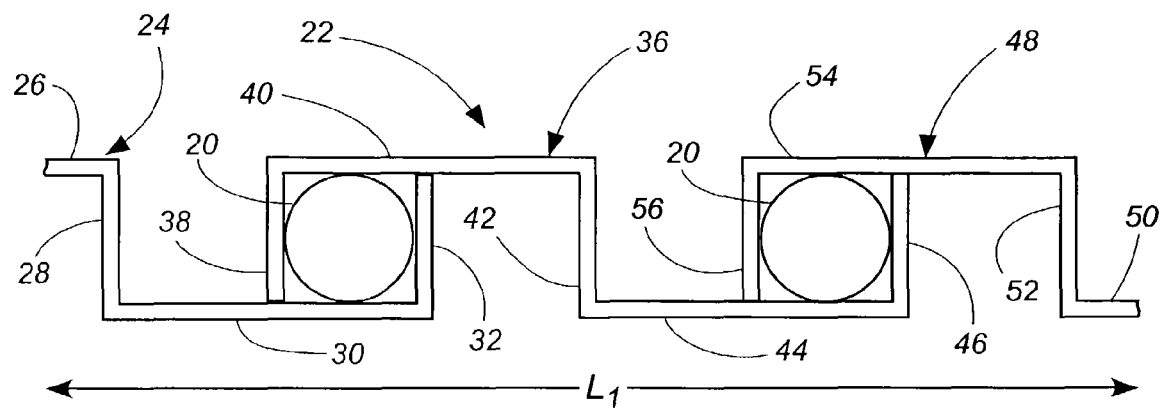
FIG. 2 is a schematic view of an inflatable cell and associated mechanical linkages of the ventricular assist device of FIG. 1, showing the cells in a deflated or deenergized condition.
Figure 3:
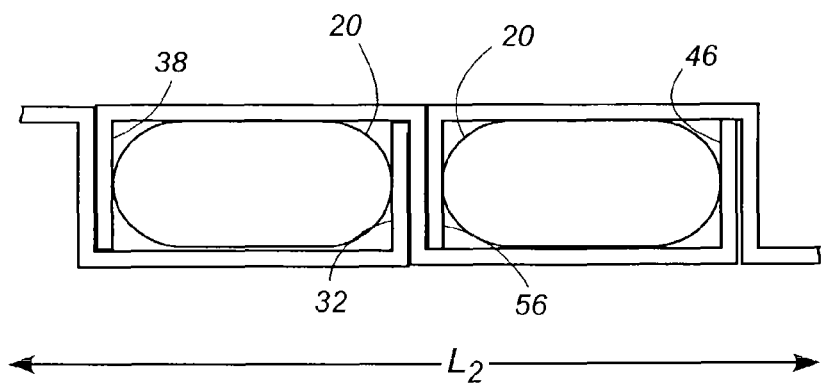
FIG. 3 is a schematic view of the inflatable cell and associated mechanical linkages of FIG. 2 showing the cells in an inflated or energized condition.

FIGS. 2 and 3 are schematic diagrams illustrating how the expansion of unit cells 20 can cause an associated mechanical linkage 22 to contract. The unit cells 20 are fluid-impervious membranes of a biocompatible elastic material. In this example the mechanical linkage 22 comprises a first connector 24, a second connector 36, and a third connector 48. The first connector 24 comprises a first end leg 26, a downturned leg 28, a horizontal wall 30, and an upturned leg 32. Coupled with the first connector 24 is the second connector 36. The second connector 36 includes a first end wall 38, an upper horizontal wall 40, an intermediate vertical wall 42, a lower horizontal wall 44, and a second end wall 46. Coupled with the opposite end of the second connector 36 is the third connector 48 which has a first end leg 50, an upturned leg 52, a horizontal wall 54, and a downturned leg 56.

Looking first at FIG. 2, it will be seen that the first unit cell 20 is located between the upturned leg 32 of the first connector 24 and the first end wall 38 of the second connector 36. Similarly, the second unit cell 20 is located between the downturned leg 56 of the third connector 48 and the second end wall 46 of the second connector 36. In FIG. 2 the unit cells 20 are deflated or deenergized, i.e., they have no hydraulic fluid in them. The linkage in FIG. 2 has a length L1.

In FIG. 3 the unit cells 20 have been inflated by the infusion of hydraulic fluid. As the unit cells expand, the upturned leg 32 of the first connector 24 is displaced away from the first end wall 38 of the second connector 36, and the downturned leg 56 of the third connector 48 is displaced away from the second end wall 46 of the second connector 36. The result of this displacement is that the overall length $L_2$ of the mechanical linkage has decreased by an amount equal to the combined increase in diameter of the two unit cells 20. In other words, $L_2$ is substantially shorter than $L_1$.

In summary, to create a mechanical device that contracts in size in response to the expansion of an inflatable member therewithin, the device should have a first non-extensible member having a first end and a cell-contacting portion contacting the cell on a side opposite the first end, and a second non-extensible member having a first end and a cell-contacting portion contacting the cell on the same side as the first end of the first structural member, so that the cell-contacting portions of the first and second non-extensible members are on generally opposite sides of the cell. Thus when the cell is expanded, such as by the infusion of a hydraulic fluid, the cell-contacting portions will be displaced apart from one another, with the consequence that the first ends of the non-extensible members will be drawn toward one another, thereby contracting the device.

It will be understood that such unit cells may be linked together to form chains of longer length, thereby increasing the amount by which the device will contract when actuated, assuming all of the unit cells are energized simultaneously. This action effectively duplicates the shortening movement of a muscle fiber.

Figure 4:
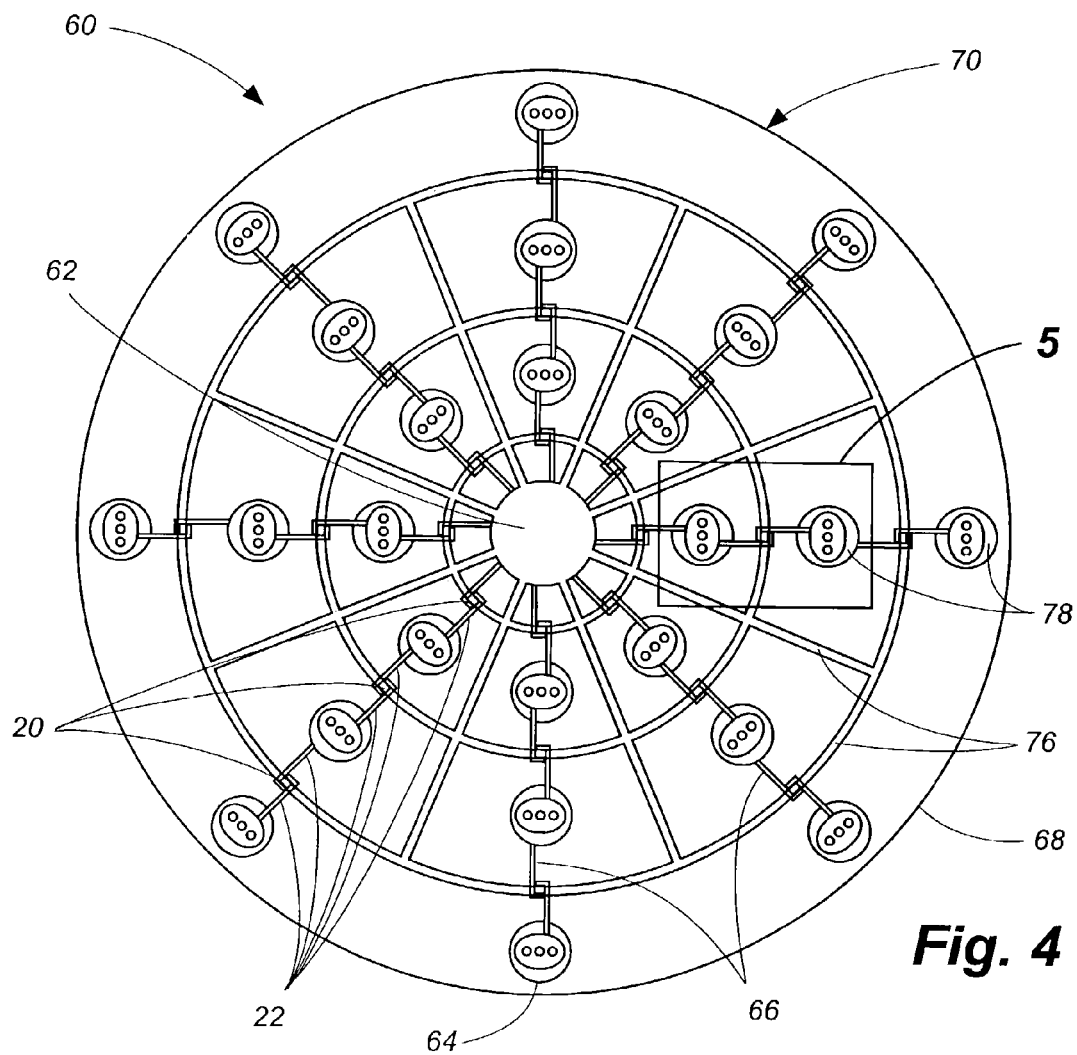
FIG. 4 is a top view of a disclosed embodiment of a ventricular assist device according to the present invention, showing the device in a deflated or deenergized condition.
Figure 5:
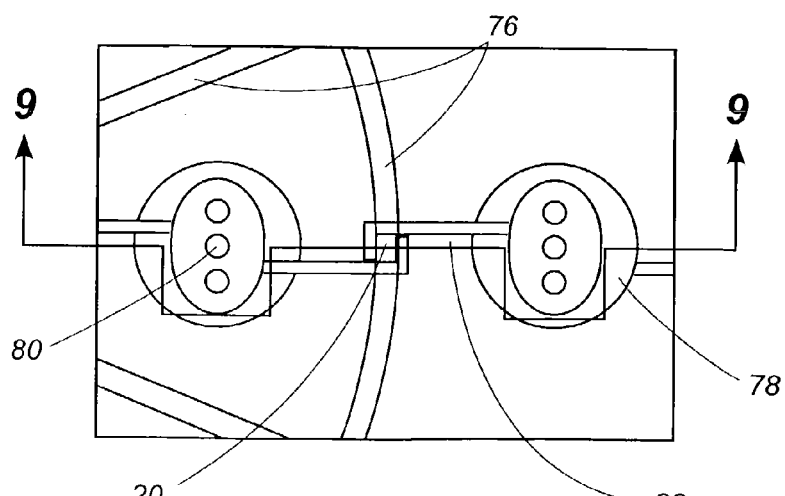
FIG. 5 is an enlarged view of the portion of FIG. 4 indicated by the box 5.
Figure 6:
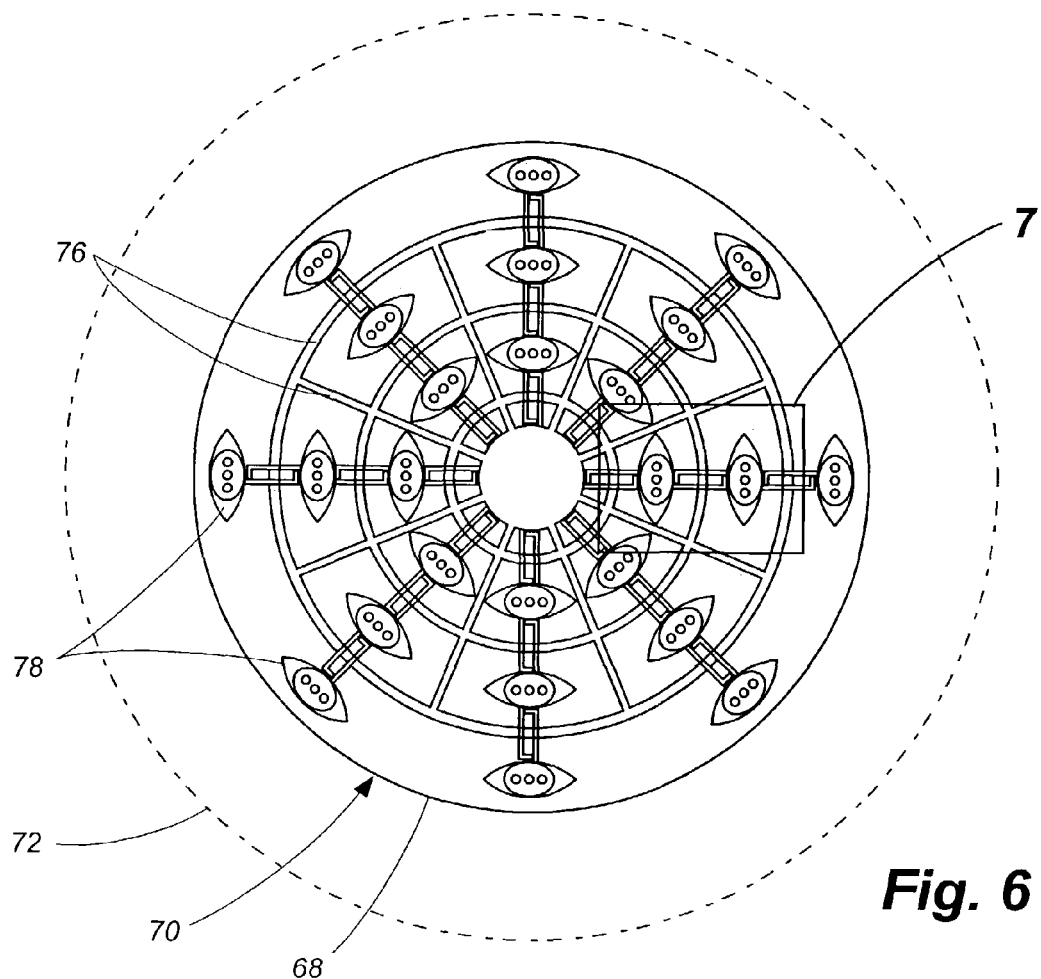
FIG. 6 is a top view of the ventricular assist device of FIG. 4 showing the device in an inflated or energized condition.
Figure 7:
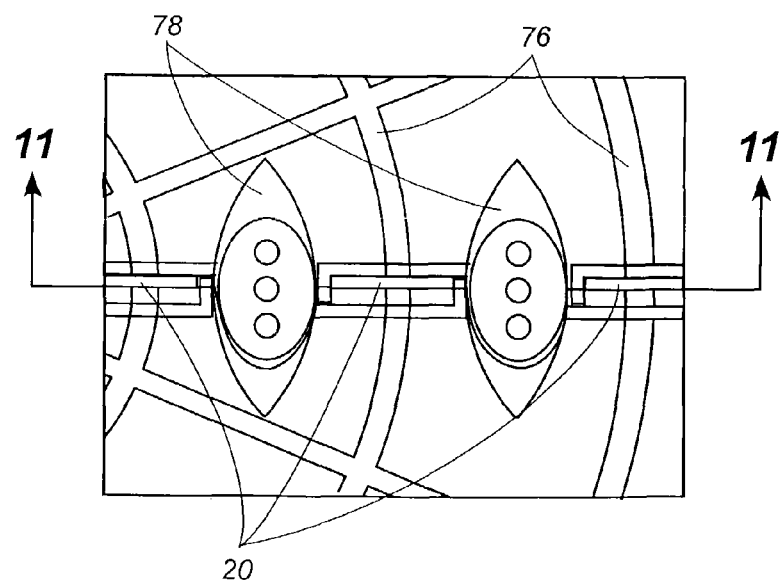
FIG. 7 is an enlarged view of the portion of FIG. 6 indicated by the box 7.
Figure 8:
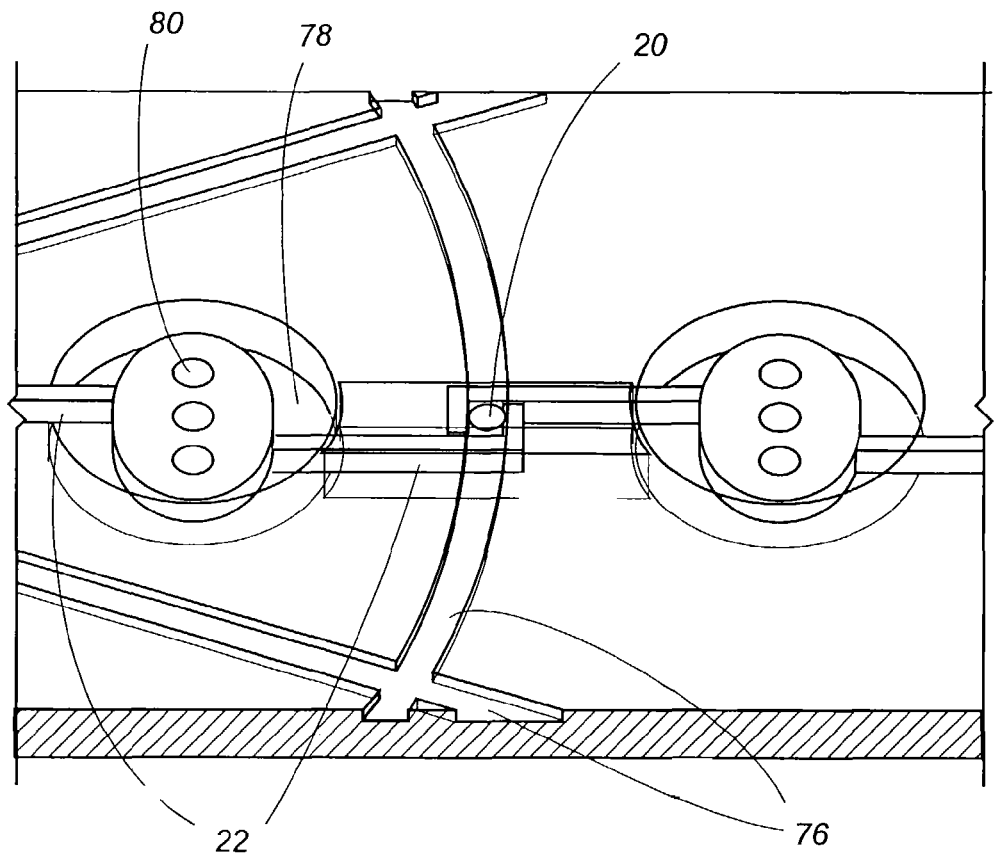
FIG. 8 is a perspective view of a unit cell and associated mechanical linkages of the ventricular assist device of FIG. 4.
Figure 9:
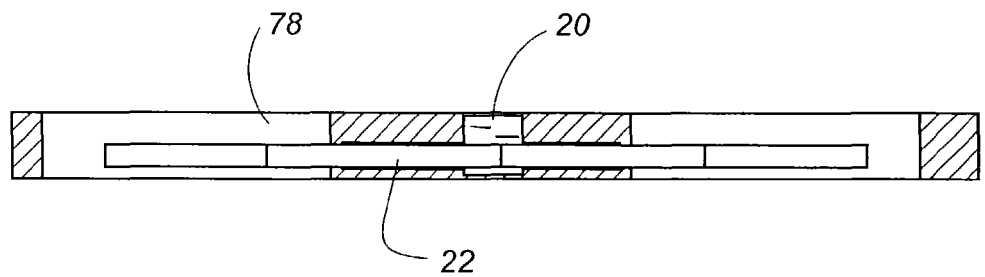
FIG. 9 is a cross-sectional view taken along section line 9-9 of FIG. 5.
Figure 10:
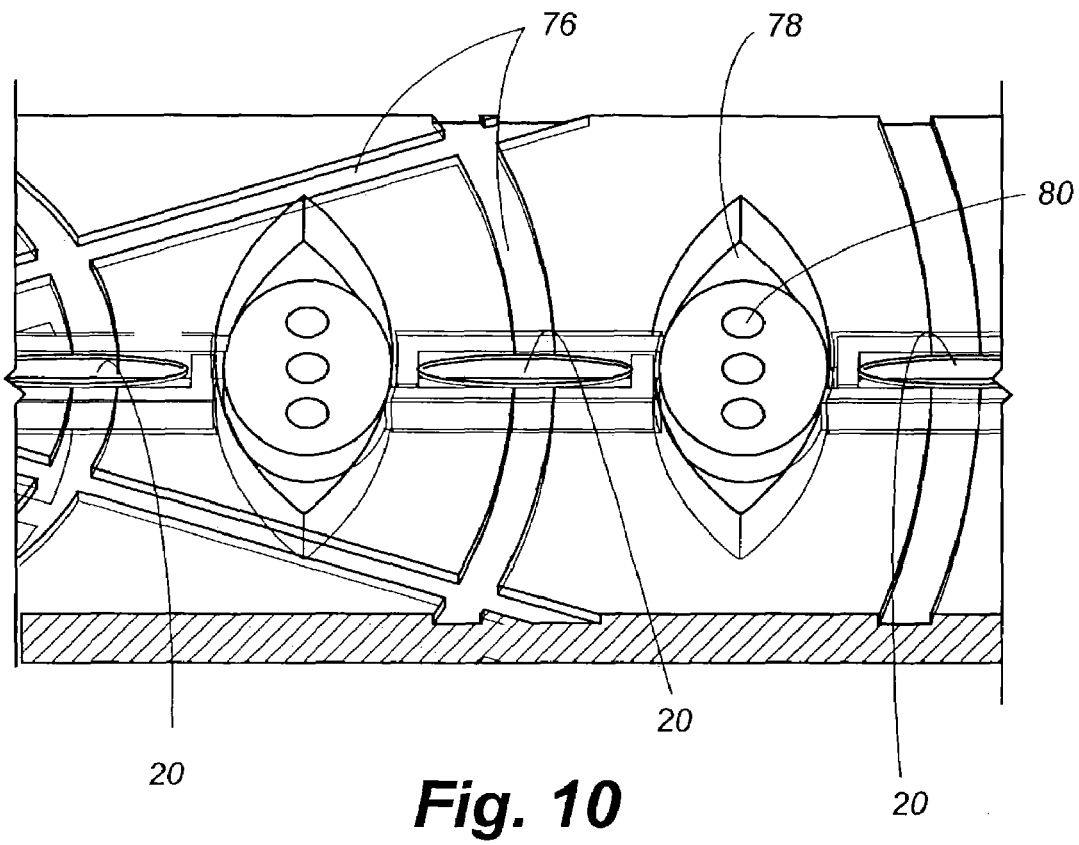
FIG. 10 is a perspective view of a unit cell and associated mechanical linkages of the ventricular assist device of FIG. 6.
Figure 11:
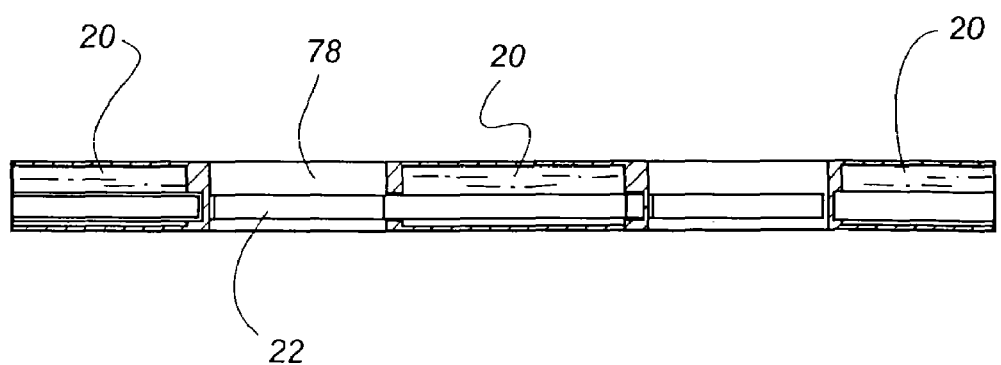
FIG. 11 is a cross-sectional view taken along section line 11-11 of FIG. 7.

Reference is now made to FIGS. 4-11 as an exemplary embodiment of a ventricular assist device 60 will now be described. As is shown in FIG. 4, the embodiment 60 comprises several chains of these linked unit cells 20 and associated mechanical linkages 22 joined to a central point 62 at one end and radially arranged so that the opposite ends 64 of the chains 66 are equally spaced along a circle 68 of particular radius. This arrangement of unit cells 20 and mechanical linkages 22 can be used to form a circular sheet 70 that can be attached to the surface of a heart 10 (FIG. 1). If the cells 20 are empty, as shown in FIG. 4, the radius of the circle 68 will be at a maximum, and the sheet 70 will provide no force on the surface of the heart. If the central chambers of the unit cells 20 are pressurized, as shown in FIG. 6, the sheet 70 will contract radially and exert an inward force to the portions of the heart to which it is attached. The dashed line 72 in FIG. 6 indicates the expanded, or relaxed, radius of the sheet 66.

A system of channels 76 within the sheet 70 has the ability to either supply pressurized fluid to each of the unit cells 20 or allow drainage of fluid from them. The actuation of the hydraulic sheet 70 can be coordinated with the natural rhythm of the heart. This can be achieved by having a sensor that can supply a signal that indicates the onset of the natural contraction of the heart, as, known in the art. This signal can then be supplied to a control system that directs the pumping mechanism to pump fluid to the unit cells 20 by way of the network of channels 76.

Cutouts 78 are provided between radially adjacent unit cells 20 to facilitate radial contraction of the device.

Provision to fasten the device to the heart in order to transfer the hydraulically-communicated mechanical energy from the ventricular assist device to the heart is included. Such features include suture points 80 in the rigid and other sections of the device 60, and provision for windows in the embedding skin to expose the suture points (and also to have the beneficial attribute to alter the mechanical properties of the skin as a function of position).

Dimensions of the device are not constrained by any particular limitation, but in a typical left-ventricular assist device application dimensions might range from 20-100 mm in diameter in its relaxed, deenergized state, and might have an energized contraction to approximately 20-50% of its deenergized state, and might have a thickness of 3-4 mm.

The device has the property that if hydraulic power or control of the valves is lost the cells 20 will return to their emptied states. In this state, the sheet 70 will be in a "rest" state, and no active forces will be applied to the heart.

Although a two-dimensional radial arrangement is indicated in FIGS. 4-11 as a specific embodiment, it should be noted that no particular restriction to two-dimensionality exists within the contemplated microhydraulic framework. Such multidimensionality may be attractive in more advanced implementations of the ventricular assist device, for example, to more closely mimic the true action of heart muscle. Multidimensional approaches to manufacturing will be discussed below.

A particular sequence of unit cell actuation can be prescribed by designing a fluid system that has channels 76 with varying cross-sectional areas and lengths. The combination of cross-sectional area combined with the total path length of the fluid to the cavities of the unit cells 20 will determine a time constant for the pressurization of each unit cell after the onset of pressurization of the device through its main inlet port.

Figure 12:
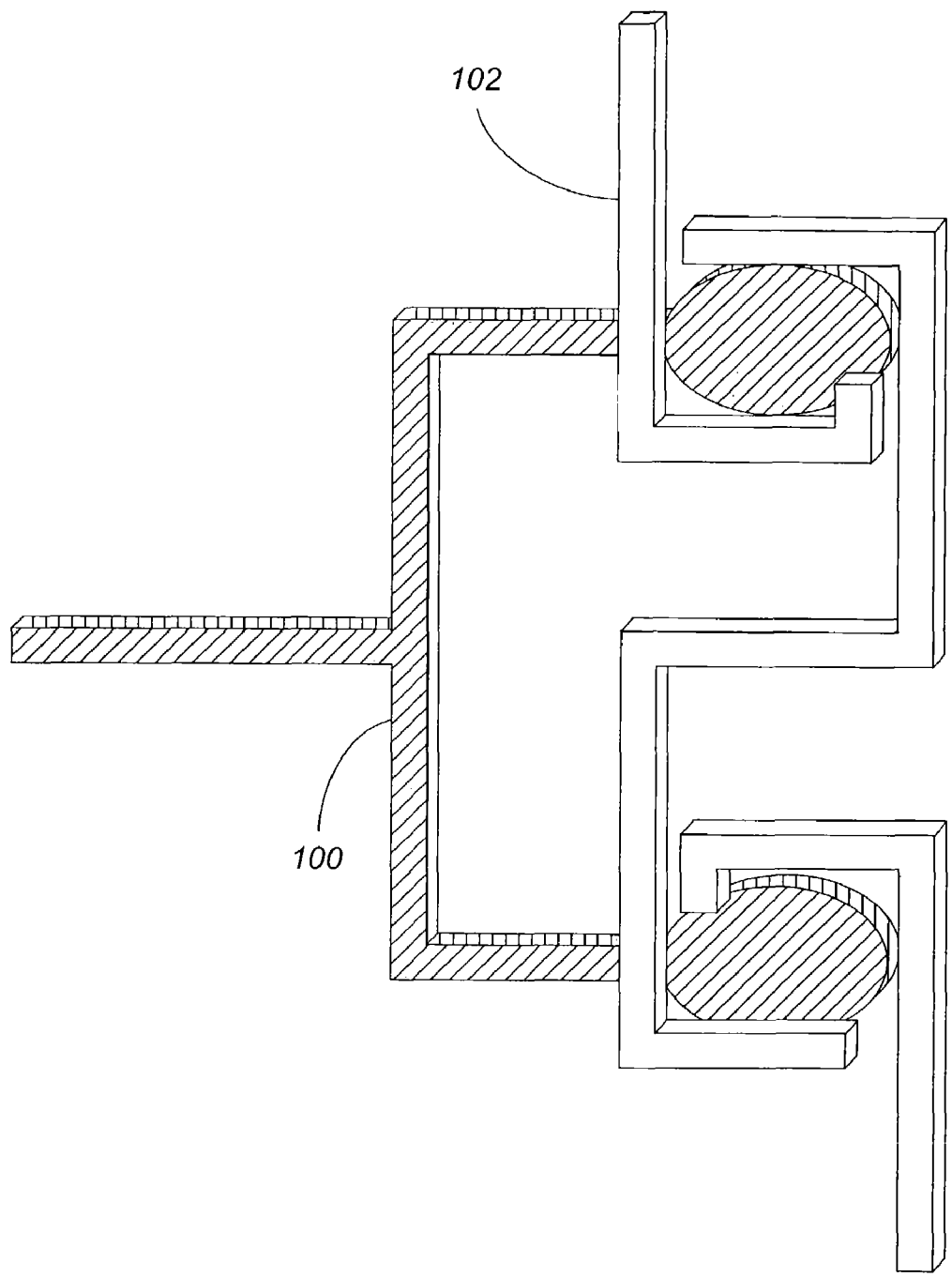
FIG. 12 is a schematic diagram illustrating a first step in manufacturing a ventricular assist device according to the present invention.
Figure 13:
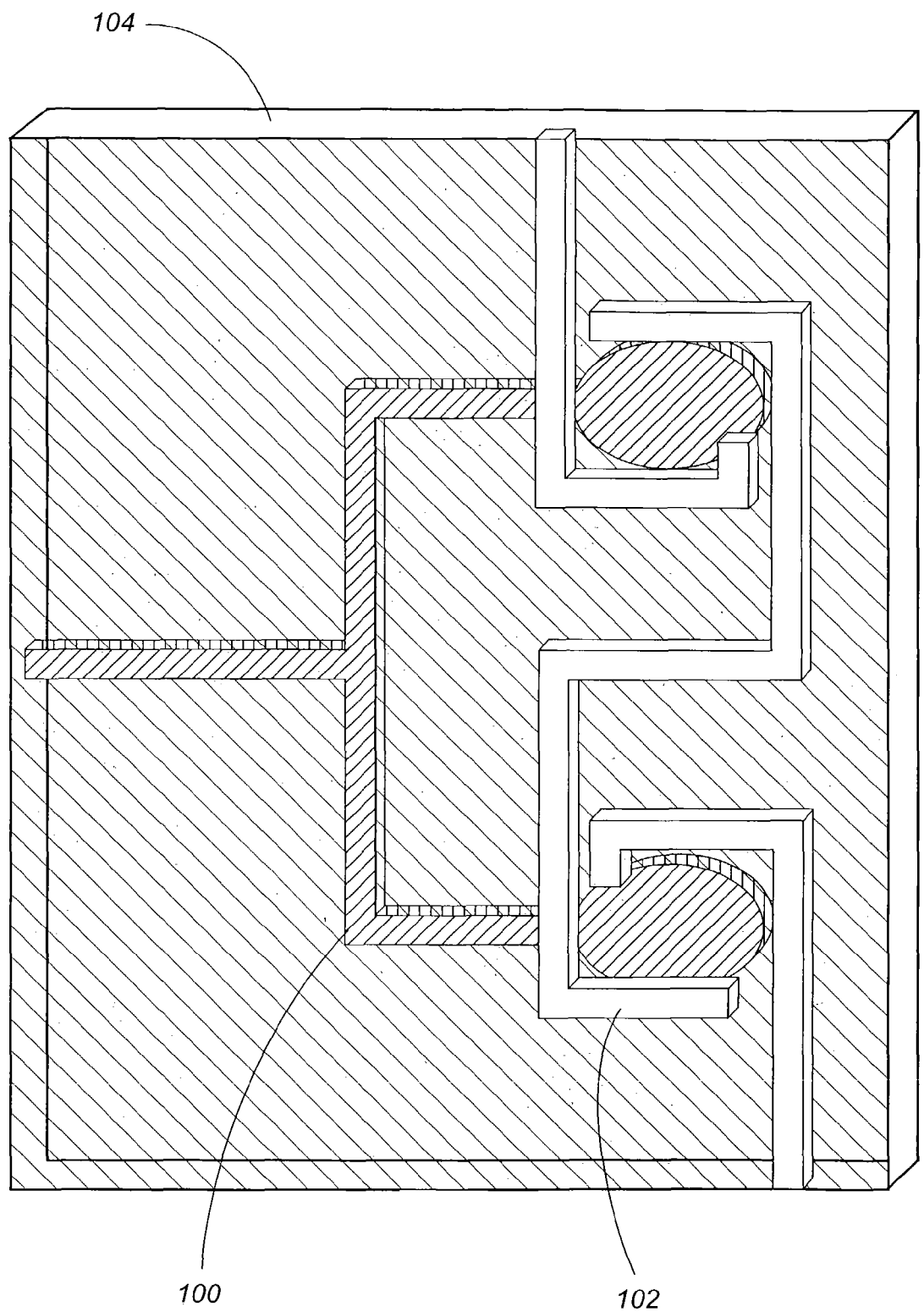
FIG. 13 is a schematic diagram illustrating a second step in manufacturing a ventricular assist device according to the present invention.
Figure 14:
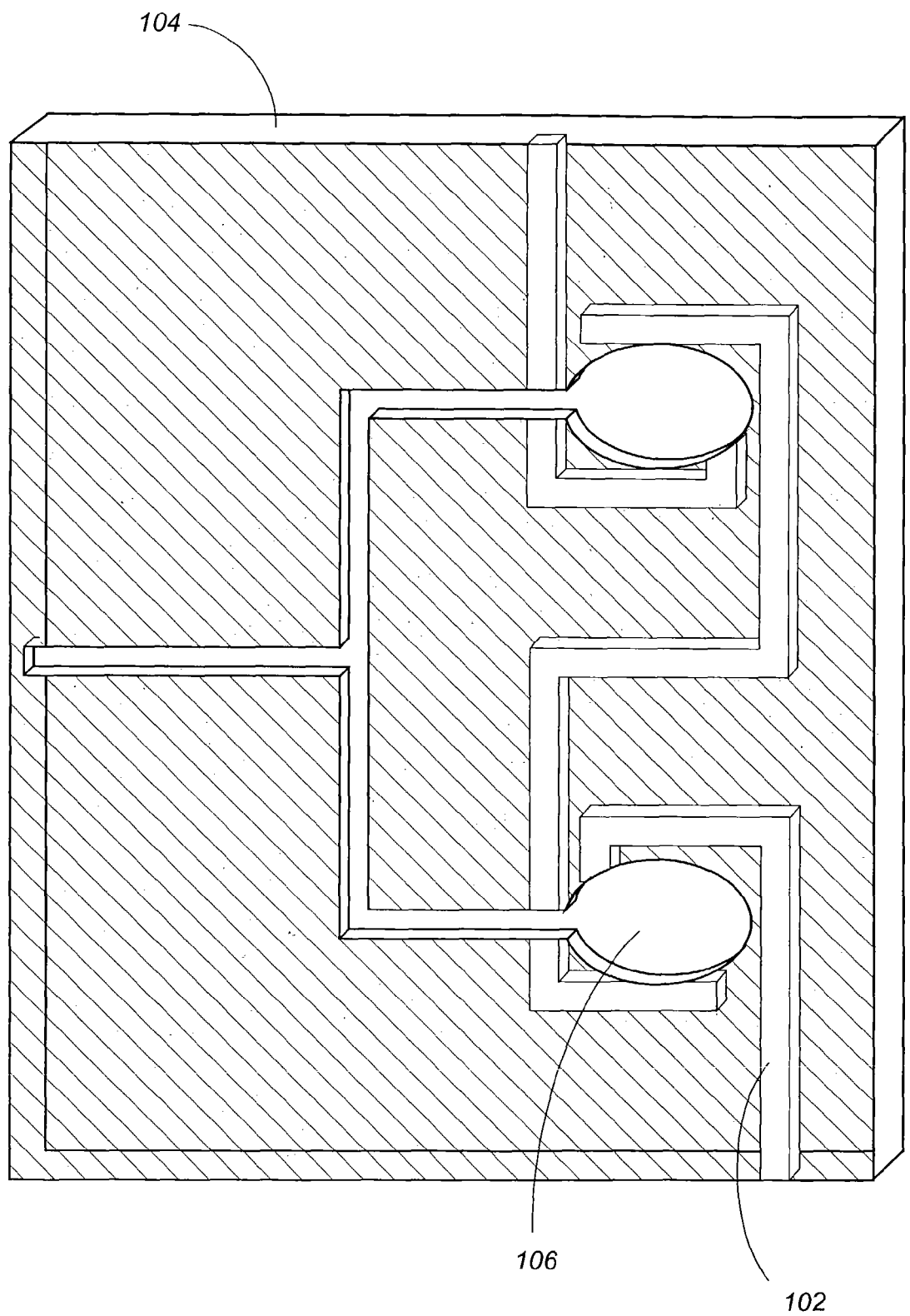
FIG. 14 is a schematic diagram illustrating a third step in manufacturing a ventricular assist device according to the present invention.

Several approaches exist for the manufacture of the skin. For example, cavities, hydraulic passages, and interconnections could be formed in individual laminate layers and the layers laminated together as known in the art to form a microhydraulic structure of substantial three-dimensional complexity. However, the extreme requirements on reliability of the device (e.g., in excess of 400 million hydraulic cycles in a typical long-term application) may preclude the use of manufacturing technologies where excessive numbers of joints and adhesive bonds are formed. A more desirable structure is one in which the flexible material of the skin with all of its three-dimensional complexity is formed as a single, integral whole. Such approaches are possible using extensions of current micromachining techniques. For example, additive or subtractive micromachining techniques can be used to create a millimeter-scale interconnect network of two dissimilar materials, a first material 100 and a second material 102 (FIG. 12). The first material 100 has the property that it can be removed selectively using chemical, thermal, or other means in the presence of the second material as well as the material which will ultimately form the skin. The second material 102 has the property that it can form the rigid elements which will ultimately remain embedded within the skin and prescribe its kinematic motion. This network can then be immersed or cured within an elastomeric or other material 104 which will form the body of the artificial muscle (FIG. 13). Upon curing or otherwise forming the muscle body material 104, advantage is taken of the fact that each central actuation cavity must ultimately be in hydraulic communication with a common fluid channel to remove the first material 100, using chemical (e.g., wet etching) or thermal means. FIG. 14 shows the completed device after selective removal of the sacrificial material 100 to form the network 106 of fluidic channels and common fluidic channel. Rigid elements 102 remain embedded in the body 104 of the artificial muscle.

In some applications, it may be desirable not to utilize elastomeric materials (which may have difficulty maintaining the extreme reliability required) but instead to utilize non-elastomeric, inflatable bladders or "bags" of highly durable material such as PEEK (poly-ether-ether-ketone) or other ultrareliable materials known in the medical art. The incorporation of these materials into the manufacturing process described above is straightforward, and can be accomplished by surrounding the first material 100 in FIG. 12 with the ultrareliable material prior to the immersion in the embedding skin as in FIG. 13. This would result in the structure of FIG. 14, with the exception that the fluidic channels would be lined with ultrareliable, pressurizable material which would potentially extend the working life of the device.

Finally, it will be understood that the preferred embodiment has been disclosed by way of example, and that other modifications may occur to those skilled in the art without departing from the scope and spirit of the appended claims.

What is claimed is:

1. A device for implanting onto the heart to assist in the normal contraction of the heart, comprising:
   a sheet of flexible base material for affixing over a diseased portion of a heart;
   a plurality of cells operatively associated with said sheet of flexible base material;
   a system of mechanical linkages operatively associated with said sheet of flexible base material and said plurality of cells such that expansion of said cells causes said mechanical linkages to shorten, thereby causing said sheet of flexible base material to contract;
   a network of conduits operatively associated with said sheet of base material for transmitting hydraulic fluid to said cells so as to cause them to expand;
   a sensor to sense the onset of a heart contraction; and
   a pump responsive to said sensed onset of a heart contraction to deliver hydraulic fluid to said plurality of cells through said network of conduits to cause said cells to expand, thereby causing said sheet of flexible base material to contract.

2. The device of claim 1, wherein said plurality of cells are embedded within said sheet of flexible base material.

3. The device of claim 1, wherein said plurality of cells comprise chambers formed within said sheet of flexible base material.

4. The device of claim 1, wherein said network of conduits operatively associated with said sheet of base material for transmitting hydraulic fluid to said cells comprises a network of passages formed within said sheet of flexible base material.

5. The device of claim 1, further comprising a plurality of holes formed in one of said base material or said mechanical linkages to provide a means by which said device can be sutured to the heart.

6. The device of claim 1, wherein said sheet of flexible base material has voids formed therein to facilitate contraction of said device.

7. The device of claim 1, wherein when said pump is not actuated to deliver hydraulic fluid to said plurality of cells, said sheet of flexible base material returns to a normal, uncontracted state, whereby if a hydraulic failure should occur, said device will not place a load on the heart.

8. A device for implanting onto the heart to assist in the normal contraction of the heart, comprising:
- a sheet of flexible base material for affixing over a diseased portion of a heart;
- a first cell operatively associated with said sheet of flexible base material;
- a first connector having a first end and an intermediate portion, said intermediate portion of said first connector being fixed with respect to said sheet of flexible material, and said first end of said first connector comprising a cell-contacting portion operatively associated with said first cell on a side opposite the intermediate portion of the first connector,
- a second connector having a first end, a second end, and an intermediate portion, said intermediate portion of said second connector being fixed with respect to said sheet of flexible material, and said first end of said second connector comprising a first cell-contacting portion operatively associated with said first cell on a side opposite the intermediate portion of the second connector, so that the cell-contacting portions of the first and second connectors are on generally opposite sides of said first cell;
- a network of conduits operatively associated with said sheet of base material for transmitting hydraulic fluid to said first cell so as to cause it to expand;
- a sensor to sense the onset of a heart contraction; and
- a pump responsive to said sensed onset of a heart contraction to deliver hydraulic fluid to said first cell through said network of conduits to cause said first cell to expand,
- wherein when said first cell is expanded, the cell-contacting portions of said first and second connectors will be displaced apart from one another such that the intermediate portion of said second connector is drawn toward said intermediate portion of said first connector, thereby contracting the device.

9. The device of claim 8, further comprising a second cell and a third connector, and
- wherein said second end of said second connector comprises a second cell-contacting portion contacting said second cell on a side opposite the intermediate portion of said second connector; and
- wherein said third connector has a first end and an intermediate portion, said first end comprising a first cell-contacting portion operatively associated with said second cell on a side opposite the intermediate portion of the third connector, so that the second cell-contacting portion of the second connector and the first cell-contacting portion of said third connector are on generally opposite sides of said second cell, and
- wherein said pump is further responsive to said sensed onset of a heart contraction to deliver hydraulic fluid to said second cell through said network of conduits to cause said second cell to expand,
- whereby when said second cell is expanded, the first cell-contacting portions of said second and third connectors will be displaced apart from one another such that the intermediate portion of said third connector is drawn toward said intermediate portion of said first connector, thereby contracting the device.

10. The device of claim 8, wherein said cell is embedded within said sheet of flexible base material.

11. The device of claim 8, wherein said cell comprises a chamber formed within said sheet of flexible base material.

12. The device of claim 8, wherein said network of conduits operatively associated with said sheet of base material for transmitting hydraulic fluid to said cell comprises a network of passages formed within said sheet of flexible base material.

13. The device of claim 8, further comprising a plurality of holes formed in one of said base material or said connectors to provide a means by which said device can be sutured to the heart.

14. The device of claim 8, wherein said sheet of flexible base material has voids formed therein to facilitate contraction of said device.

15. The device of claim 8, wherein when said pump is not actuated to deliver hydraulic fluid to said plurality of cells, said sheet of flexible base material returns to a normal, uncontracted state, whereby if a hydraulic failure should occur, said device will not place a load on the heart.

16. A device for implanting onto the heart to assist in the normal contraction of the heart, comprising:
- a sheet of flexible base material for affixing over a diseased portion of a heart;
- a plurality of cells operatively associated with said sheet of flexible base material and arranged in a generally linear configuration;
- a plurality of connectors each having a midpoint and first and second ends, said first end of each of said connectors comprising a first cell-contacting portion, said second end of each of said connectors comprising a second cell-contacting portion, and each one of said connectors being arranged such that said first and second cell-contacting portions contact adjacent cells on the side of said cells opposite said midpoint of said one connector;
- a network of conduits operatively associated with said sheet of base material for transmitting hydraulic fluid to said cells so as to cause them to expand;
- a sensor to sense the onset of a heart contraction; and
- a pump responsive to said sensed onset of a heart contraction to deliver hydraulic fluid to said cells through said network of conduits to cause said cells to expand.

17. The device of claim 16, wherein said plurality of connectors forms a chain, and wherein said device comprises a plurality of said chains.

18. The device of claim 17, wherein said plurality of chains are radially arranged on said base material emanating from a common center.

19. The device of claim 16, wherein when said pump is not actuated to deliver hydraulic fluid to said plurality of cells, said sheet of flexible base material returns to a normal, uncontracted state, whereby if a hydraulic failure should occur, said device will not place a load on the heart.

20. An apparatus for implanting onto a ventricle to assist in the normal contraction of the heart, comprising:
- a sheet being selectively hydraulically actuatable to contract, and wherein said sheet of hydraulically actuatable material comprises:
  - a plurality of cells operatively associated with said sheet;
  - a system of mechanical linkages operatively associated with said sheet and said plurality of cells such that expansion of said cells causes said mechanical linkages to shorten, thereby causing said sheet to contract; and a network of conduits operatively associated with said sheet for transmitting hydraulic fluid to said cells so as to cause them to expand;

a sensor to sense the onset of a heart contraction; and a pump responsive to said sensed onset of a heart contraction to deliver hydraulic fluid to said sheet to cause said sheet to contract, whereby when said apparatus is implanted onto a ventricle and the onset of a heart contraction is sensed, the ventricle will be assisted in contraction; and whereby when said apparatus is implanted onto a ventricle and the onset of a heart contraction is sensed, said pump delivers hydraulic fluid through said network of conduits to said plurality of cells, causing said cells to expand, thereby causing said mechanical linkages to shorten, and thereby causing said sheet to contract.

21. The apparatus of claim 20, wherein said plurality of cells are embedded within said sheet.

22. The apparatus of claim 20, wherein said plurality of cells comprise chambers formed within said sheet.

23. The apparatus of claim 20, further comprising a plurality of holes formed in one of said sheet or said mechanical linkages to provide a means by which said device can be sutured to the ventricle.

* * * * *